United States Patent
Steiner et al.

(10) Patent No.: US 6,458,821 B1
(45) Date of Patent: Oct. 1, 2002

(54) N-SUBSTITUTED AZABICYCLOHEPTANE DERIVATIVES, PRODUCTION AND USE THEREOF

(75) Inventors: Gerd Steiner, Kirchheim; Thomas Höger, Edingen-Neckarhausen; Liliane Unger, Ludwigshafen; Hans-Jürgen Teschendorf, Dudenhofen; Frieder Juchelka, Leimen, all of (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/762,046

(22) Filed: Feb. 1, 2001

(30) Foreign Application Priority Data

Aug. 12, 1998 (DE) .......................... 198 36 404
Feb. 9, 2000 (DE) .......................... 100 05 942

(51) Int. Cl.$^7$ ................... A61K 31/4184; C07D 403/06
(52) U.S. Cl. ................... 514/387; 548/305.1
(58) Field of Search ................ 548/305.1; 514/387

(56) References Cited

U.S. PATENT DOCUMENTS

| | | | |
|---|---|---|---|
| 4,254,127 A | 3/1981 | Vandenbeck et al. | 424/263 |
| 5,475,105 A | * 12/1995 | Steiner et al. | 544/48 |
| 6,028,073 A | * 2/2000 | Steiner et al. | 514/258 |

FOREIGN PATENT DOCUMENTS

| | | |
|---|---|---|
| WO | WO 94/00431 | 1/1994 |
| WO | WO 94/00458 | 1/1994 |
| WO | WO 95/15312 | 6/1995 |
| WO | WO 96/04245 | 2/1996 |
| WO | WO 96/04272 | 2/1996 |

OTHER PUBLICATIONS

Vernin et al. "Synthesis of 1–Alkyl and 1,3–Dialkyl–2–Benzimidazalones from 1–Alkenyl–2_Benzimidazolones using Phase–Transfer Catalysts Technique" J. Heterocyclic Chem. vol. 18 (1985) pp. 85–89.
Steiner et al. "Diastereoselective Synthesis of Exo–6–Aryl–3–Aza–Bicyclo [3,2,0]Heptane Derivatives by Intramolecular [2+2] Photocycloadditions of Diallyic Amines" Heterocycles vol. 40, (1995) pp. 319–350.
H.Sucker et al. "Hilfsstoffe für Arzneiformen" Pharm. Technologies (1978) pp. 280–360.

* cited by examiner

*Primary Examiner*—Laura L. Stockton
(74) *Attorney, Agent, or Firm*—Keil & Weinkauf

(57) ABSTRACT

Compounds of the formula

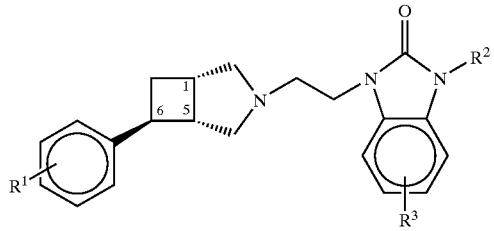

in which $R^1$, $R^2$ and $R^3$ have the meanings stated in the description, are described.

The novel substances are suitable for controlling diseases.

10 Claims, No Drawings

N-SUBSTITUTED AZABICYCLOHEPTANE DERIVATIVES, PRODUCTION AND USE THEREOF

This application is a 371 of PCT/EP99/05166 filed Jul. 20, 1999.

The invention relates to novel N-substituted azabicycloheptane derivatives, their preparation and use for controlling diseases.

Exo-6-phenyl-3-azabicyclo[3.2.0]heptane deriviates have interesting properties as potential neuroleptics (WO 94/00458, WO 95/15312). Of particular importance in this connection are the observed high affinities for $D_4$ and $5-HT_2$ receptors.

The most interesting substance from the above class of compounds with high $D_4/5-HT_{2A}$ affinity and good selectivity versus $D_2$ is (+)-(1S,5R,6S)-exo-3-[2-[6-(4-fluorophenyl)-3-azabicyclo[3.2.0]-heptan-3-yl]ethyl]-1H,3H-quinazoline-2,4-dione (=substance A), which is a potential neuroleptic. However, there is an upper limit to dosage of substance A due to prolongations which occur in the QT interval in the ECG.

We have now found substances with better properties.

The invention relates to N-substituted 3-azabicyclo[3.2.0]-heptane derivatives of the formula I

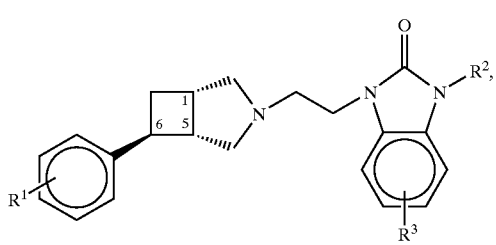

in which $R^1$ is fluorine or chlorine, $R^2$ is $C_1$–$C_3$-alkyl or cyclopropyl, and $R^3$ is hydrogen, fluorine or chlorine, and the salts thereof with physiologically tolerated acids.

Preferred compounds are those in which $R^1$ is chlorine, preferably in the p position, $R^2$ is methyl or cyclopropyl and $R^3$ is hydrogen.

The following compounds are to be mentioned as particularly preferred:

(+)-(1S,5R,6S)-exo-1-[2-[6-(4-chlorophenyl)-3-azabicyclo[3.2.0]-heptan-3-yl]ethyl]-3-methyl-2H-1,3-dihydrobenzimidazol-2-one, (+)-(1S,5R,6S)-exo-1-[2-[6-(4-chlorophenyl)-3-azabicyclo[3.2.0]-heptan-3-yl]ethyl]-3-ethyl-2H-1,3-dihydrobenzimidazol-2-one, and (+)-(1S,5R,6S)-exo-1-[2-[6-(4-fluorophenyl)-3-azabicyclo[3.2.0]-heptan-3-yl]ethyl]-3-cyclopropyl-2H-1,3-dihydrobenzimidazol-2-one.

The compounds of the formula I according to the invention can be prepared by reacting a compound of the formula II

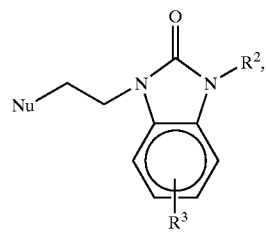

in which $R^2$ and $R^3$ have the abovementioned meanings, and in Nu is a nucleofugic leaving group, with a 3-azabicyclo[3.2.0]heptane derivative of the formula III as (+)-(1S,5R,exo-6S) enantiomer

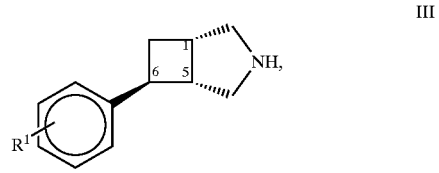

in which $R^1$ has the abovementioned meaning, and converting the compound obtained in this way where appropriate into the acid addition salt with a physiologically tolerated acid.

Suitable and preferred nucleofugic leaving groups for Nu are halogen atoms, in particular bromine or chlorine.

The reaction expediently takes place in the presence of an inert base such as triethylamine or potassium carbonate as acid acceptor in an inert solvent such as a cyclic saturated ether, in particular tetrahydrofuran or dioxane, or a benzenoid hydrocarbon such as toluene or xylene.

The reaction generally takes place at temperatures from 20 to 150° C., in particular from 80 to 140° C., and is generally complete within 1 to 10 hours.

The compounds of the formula I according to the invention can be purified either by recrystallization from conventional organic solvents, preferably from a lower alcohol such as ethanol, or by column chromatography.

The free 3-azabicyclo[3.2.0]heptane derivatives of the formula I can be converted in a conventional way into the acid addition salt with a pharmacologically suitable acid, preferably by treating a solution with one equivalent of the appropriate acid. Examples of pharmaceutically suitable acids are hydrochloric acid, phosphoric acid, sulfuric acid, methanesulfonic acid, sulfamic acid, maleic acid, fumaric acid, oxalic acid, tartaric acid or citric acid.

The compounds according to the invention have valuable pharmacological properties. They can be used as neuroleptics (in particular atypical), antidepressants, sedatives, hypnotics, CNS protective agents or agents for treating cocaine dependency. It is possible for several of the types of action mentioned to occur in combination in a compound according to the invention.

The substances are characterized in particular by a very high and selective affinity for the dopamine $D_4$ and serotonin 2A receptors.

The prolongations of the QT interval measured using the model of the guinea pig papillary muscle are negligibly small. This means that the novel substances are well tolerated even at high dosages.

The invention accordingly also relates to a therapeutic composition which has a content of a compound of the formula I or its pharmacologically suitable acid addition salt as active ingredient in addition to conventional carriers and diluents, and to the use of novel compounds for controlling diseases.

The compounds according to the invention can be administered in a conventional way orally or parenterally, intravenously or intramuscularly.

The dosage depends on the age, condition and weight of the patient and on the mode of administration. The daily dose of active ingredient is usually between about 1 and 100 mg/kg of body weight on oral administration and between 0.1 and 10 mg/kg of body weight on parenteral administration.

The novel compounds can be used in conventional solid or liquid pharmaceutical forms, e.g. as uncoated or (filmcoated) tablets, capsules, powders, granules, suppositories, solutions, ointments, creams or sprays. These are produced in a conventional way. The active ingredients can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1978). The administration forms obtained in this way normally contain the active ingredient in an amount of from 1 to 99% by weight.

The substances of the formula II and III required as starting materials for synthesizing the compounds according to the invention are known (WO 94/00458; Heterocycles 40 (1), 319–330 (1995); J. Heterocyclic Chem. 18, 85–89 (1981)) or can be synthesized from analogous starting materials using the preparation methods described in the literature.

The following examples serve to illustrate the invention:
A Preparation of the Starting Materials a) 1-(α-Phenylvinyl)-2H-1,3-dihydrobenzimidazol-2-one 21.6 g (200 mmol) of o-phenylenediamine and 37 ml (214 mmol) of ethyl benzoylacetate in 75 ml of 4-tert-butyltoluene with the addition of a spatula tip of p-toluenesulfonic acid were refluxed with a water trap at a bath temperature of 200° C. under nitrogen for 1 h, and the liberated water was separated off. After cooling, 80 ml of acetonitrile were added to the reaction mixture and, after stirring in an ice bath, the solid was filtered off with suction and washed with cold acetonitrile. 39.5 g (84%) of product were isolated, melting point 167–169° C.

1-(α-Phenylvinyl)-6-chloro-2H-1,3-dihydrobenzimidazol-2-one can be prepared in an analogous manner (starting material: 4-chloro-1,2-diaminobenzene).

b) 1-(α-Phenylvinyl)-3-methyl-2H-1,3-dihydrobenzimidazol-2-one 40 ml of 10% strength sodium hydroxide solution, 0.2 g of benzyltriethylammonium chloride and 1.76 ml (18.5 mmol) of dimethyl sulfate were added to 3.5 g (14.8 mmol) of 1-(α-phenylvinyl)-2H-1,3-dihydrobenzimidazol-2-one in 70 ml of toluene, and the mixture was stirred at 60° C. for 2 h. The toluene phase was then concentrated, and 3.65 g (99%) of product were isolated as an oil with sufficient purity for the next reaction.

The following were prepared in an analogous manner: 1-(α-phenylvinyl)-3-ethyl-2H-1,3-dihydrobenzimidazol-2-one (alkylating agent: diethyl sulfate) and 1-(α-phenylvinyl)-3-n-propyl-2H-1,3-dihydrobenzimidazol-2-one (alkylating agent 1-bromopropane), 1-(α-phenyl-vinyl)-3-methyl-6-chloro-2H-1,3-dihydrobenzimidazol-2-one (starting material: 1-(α-phenylvinyl)-6-chloro-2H-1,3-dihydrobenzimidazol-2-one) and 1-(2-chloroethyl)-3-methyl-5-chloro-2H-1,3-dihydrobenzimidazol-2-one (starting material: 1-(2-chloroethyl)-5-chloro-2H-1,3-dihydrobenzimidazol-2-one).

c) 1-Methyl-2H-1,3-dihydrobenzimidazol-2-one 3.65 g (14.6 mmol) 1-(α-phenylvinyl)-3-methyl-2H-1,3-dihydrobenzimidazol-2-one were dissolved in 30 ml of ethanol and, after addition of 60 ml of 10% strength hydrochloric acid and of 10 ml of concentrated hydrochloric acid, stirred at 80° C. for 2 h. The mixture was then concentrated, and ice was added to the remaining aqueous solution. The precipitated solids were stirred while cooling in an ice bath, filtered off with suction and washed with water. 1.7 g (79%) of product were isolated.

The following were prepared analogously: 1-(2-chloroethyl)-5-chloro-2H-1,3-dihydrobenzimidazol-2-one (starting material: 1-(2-chloroethyl)-3-(α-phenylvinyl)-5-chloro-2H-1,3-dihydrobenzimidazol-2-one) and 1-methyl-5-chloro-2H-1,3-dihydrobenzimidazol-2-one (starting material: 1-(α-phenylvinyl)-3-methyl-6-chloro-2H-1,3-dihydrobenzimidazol-2-one).

d) 1-(2-Chloroethyl)-3-methyl-2H-1,3-dihydrobenzimidazol-2-one 1.7 g (11.5 mmol) of 1-methyl-2H-1,3-dihydrobenzimidazol-2-one in 40 ml of acetonitrile were mixed with 1.6 g (11.5 mmol) of finely powdered potassium carbonate and 2.9 ml (35 mmol) of 1-bromo-2-chloroethane and refluxed for 14 h. After cooling, the solids were filtered off with suction, washing with acetonitrile, and then the filtrate was concentrated. 2.3 g (95%) of product were isolated as an oil which slowly crystallized, melting point 87–89° C.

The following were prepared analogously: 1-(2-chloroethyl)-3-(α-phenylvinyl)-5-chloro-2H-1,3-dihydrobenzimidazol-2-one (starting material: 1-(α-phenylvinyl)-6-chloro-2H-1,3-dihydrobenzimidazol-2-one) and 1-(2-chloroethyl)-3-methyl-6-chloro-2H-1,3-dihydrobenzimidazol-2-one (starting material: 1-methyl-5-chloro-2H-1,3-dihydrobenzimidazol-2-one).

e) (+)-(1S,5R,6S)-exo-6-(4-Chlorophenyl)-3-azabicyclo[3.2.0]heptane

The (+) enantiomer was isolated by the method described in Heterocycles 40 (1), 326 (1995).

f) 1-(α-Phenylvinyl)-3-cyclopropyl-2H-1,3-dihydrobenzimidazol-2-one 1.35 g (45 mmol) of sodium hydride (80 percent) were added in portions to 10.0 g (42.4 mmol) of 1-(α-phenyl-vinyl)-2H-1,3-dihydrobenzimidazol-2-one in 80 ml of dimethylformamide with thorough stirring, and the reaction mixture was then stirred for 2 h. Subsequently 8.0 ml (100 mmol) of cyclopropyl bromide were added, and the reaction mixture was transferred into a 0.3 l stirred autoclave which was then heated at 200° C. for 10 h. After cooling and concentration in a rotary evaporator, the residue was partitioned between methylene chloride and water, acidifying with 10 percent hydrochloric acid. The aqueous phase was extracted once more with methylene chloride. After drying and concentration of the organic phase, 12.4 g of crude product were isolated and were purified by column chromatography (silica gel, mobile phase methylene chloride). Yield 3.6 g (31%) of adequate purity.

Preparation of the Final Products

Example 1

(+)-(1S,5R,6S)-exo-1-[2-[6-(4-Chlorophenyl)-3-azabicyclo-[3.2.0]heptan-3-yl]ethyl]-3-methyl-2H-1,3-dihydrobenzimidazol-2-one tartrate×2H₂O 2.5 g (12.1 mmol) of (+)-(1S,5R,6S)-exo-6-(4-chlorophenyl)-3-azabicyclo[3.2.0]heptane in 60 ml of xylene were mixed with 2.55 g (12.1 mmol) of 1-(2-chloroethyl)-3-methyl-2H-1,3-dihydrobenzimidazol-2-one and 1.7 g (12.1 mmol) of finely powdered potassium carbonate and refluxed for 20 h. The mixture was then concentrated in a rotary evaporator, and the residue was partitioned between water and methyl tert-butyl ether at pH 10. The aqueous phase was extracted once more with methyl tert-butyl ether, and then the combined organic phases were concentrated. The crude product was purified by column chromatography (silica gel, mobile phase methylene chloride/methanol 97/3). 3.3 g (71%) of product were isolated as an oil which was dissolved in 200 ml of ether and converted with 1.4 g (9.3 mmol) of tartaric acid, dissolved in ethanol, into the tartrate (melting point 107 to 109° C.). $[\alpha]_D=+55.4°$ (EtOH)

| Elemental analysis C₂₂H₂₄N₃OCl × C₄H₆O₆ × 2H₂O | | | | | |
|---|---|---|---|---|---|
| calculated | C 54.97 | H 6.03 | N 7.39 | O 25.34 | Cl 6.24 |
| found | C 54.9 | H 5.8 | N 7.1 | O 25.5 | Cl 6.2 |

The following were prepared in an analogous manner:

2. (+)-(1S,5R,6S)-exo-1-[2-[6-(4-Chlorophenyl)-3-azabicyclo-[3.2.0]heptan-3-yl]ethyl]-3-ethyl-2H-1,3-dihydrobenzimidazol-2-one×HCl, melting point 174 to 176° C., $[\alpha]_D=+67.7°$ (EtOH)
3. (+)-(1S,5R,6S)-exo-1-[2-[6-(4-Chlorophenyl)-3-azabicyclo-[3.2.0]heptan-3-yl]ethyl]-3-n-propyl-2H-1,3-dihydrobenzimidazol-2-one×HCl, melting point 178 to 180° C., $[\alpha]_D=+66.4°$ (EtOH)
4. (+)-(1S,5R,6S)-exo-1-[2-[6-(4-chlorophenyl)-3-azabicyclo-[3.2.0]heptan-3-yl]ethyl]-3-methyl-5-chloro-2H-1,3-dihydrobenzimidazol-2-one×HCl, melting point 101 to 103° C., $[\alpha]_D=+92.3°$ (EtOH)
5. (+)-(1S,5R,6S)-exo-1-[2-[6-(4-chlorophenyl)-3-azabicyclo[3.2.0]heptan-3-yl]ethyl]-3-methyl-6-chloro-2H-1,3-dihydrobenzimidazol-2-one×HCl, melting point 230 to 232° C., $[\alpha]_D=+77.2°$ (EtOH)
6. (+)-(1S,5R,6S)-exo-1-[2-[6-(4-chlorophenyl)-3-azabicyclo[3.2.0]heptan-3-yl]ethyl]-3-cyclopropyl-2H-1,3-dihydrobenzimidazol-2-one×HCl, melting point 109 to 111° C., $[\alpha]_D=+73.5°$ (EtOH)
7. (+)-(1S,5R,6S)-exo-1-[2-[6-(4-fluorophenyl)-3-azabicyclo[3.2.0]heptan-3-yl]ethyl]-3-cyclopropyl-2H-1,3-dihydrobenzimidazol-2-one×HCl, melting point 121 to 123° C., $[\alpha]_D=+64.5°$ (EtOH)

We claim:
1. An N-substituted 3-azabicyclo[3.2.0]heptane compound of formula I

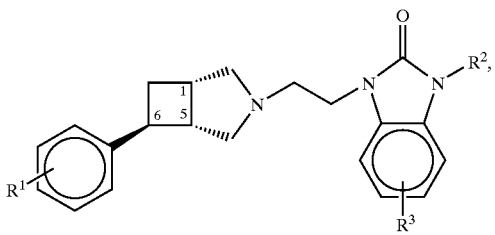

in which
R¹ is chlorine,
R² is C₁–C₃-alkyl or cyclopropyl, and
R³ is hydrogen,
or a salt thereof with a physiologically tolerated acid.
2. The compound of formula I defined in claim 1, wherein R¹ is bonded in para position of the phenyl ring.
3. The compound of formula I defined in claim 1, wherein R² is methyl or ethyl, or the salt thereof with the pysiologically tolerated acid.
4. The compound of formula I defined in claim 1, which is selected from the group consisting of
(+)-(1S,5R,6S)-exo-1-[2-[6-(4-chlorophenyl)-3-azabicyclo[3.2.0]-heptan-3-yl]ethyl]-3-methyl-2H-1,3-dihydrobenzimidazol-2-one, and
(+)-(1S,5R,6S-)-exo-1-[2-[6-(4-chlorophenyl)-3-azabicyclo[3.2.0]-heptan-3-yl]ethyl]-3-ethyl-2H-1,3-dihydrobenzimidazol-2-one.
5. The salt of the compound of formula I defined in claim 1, which is selected from the group consisting of
(+)-(1S,5R,6S)-exo-1-[2-[6-(4-chlorophenyl)-3-azabicyclo-[3.2.0]heptan-3-yl]ethyl]-3-methyl-2H-1,3-dihydrobenzimidazol-2-one tartrate×2H₂O,
(+)-(1S,5R,6S)-exo-1-[2-[6-(4chlorophenyl)-3-azabicyclo-[3.2.0]heptan-3-yl]ethyl]-3-ethyl-2H-1,3-dihydrobenzimidazol-2-one×HCl,
(+)-(1S,5R,6S)-exo-1-[2-[6-(4-chlorophenyl)-3-azabicyclo-[3.2.0]heptan-3-yl]ethyl]-3-n-propyl-2H-1,3-dihydrobenzimidazol-2-one×HCl,
(+)-(1S,5R,6S)-exo-1-[2-[6-(4-chlorophenyl)-3-azabicyclo-[3.2.0]heptan-3-yl]ethyl]-3-methyl-5-chloro-2H-1,3-dihydrobenzimidazol-2-one×HCl,
(+)-(1S,5R,6S)-exo-1-[2-[6-(4-chlorophenyl)-3-azabicyclo-[3.2.0]heptan-3-yl]ethyl]-3-methyl-6-chloro-2H-1,3-dihydrobenzimidazol-2-one×HCl, and
(+)-(1S,5R,6S)-exo-1-[2-[6-(4-chlorophenyl)-3-azabicyclo-[3.2.0]heptan-3-yl]ethyl]-3-cyclopropyl-2H-1,3-dihydrobenzimidazol-2-one×HCl.
6. A pharmaceutical composition comprising an effective amount of the compound of formula I defined in claim 1 and at least one conventional carrier or diluent.
7. A method of treating a patient in need of such treatment with a neuroleptic, antidepressant, sedative, hypnotic, CNS protective agent or an agent for the treatment of cocaine dependency, which comprises administering to said patient an effective amount of the compound of formula I defined in claim 1.
8. The method of claim 7, wherein the compound of formula I is used as a neuroleptic.
9. The method of claim 7, wherein the compound of formula I is administered to the patient orally in a daily dose of from 1 to 100 mg per kg body weight of the patient.
10. The method of claim 7, wherein the compound of formula I is administered to the patient parenterally in a daily dose of from 0.1 to 10 mg per kg body weight of the patient.

* * * * *